(12) United States Patent
Goldberg et al.

(10) Patent No.: US 8,808,278 B2
(45) Date of Patent: Aug. 19, 2014

(54) PATIENT SIDE SYSTEMS WITH A COUNTERBALANCE SUBSYSTEM

(75) Inventors: Randal P. Goldberg, Fremont, CA (US); Henry Hazebrouck, Sunnyvale, CA (US); Dean Hoornaert, San Jose, CA (US); David Lidgey, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 18 days.

(21) Appl. No.: 13/181,271

(22) Filed: Jul. 12, 2011

(65) Prior Publication Data

US 2012/0179166 A1 Jul. 12, 2012

Related U.S. Application Data

(62) Division of application No. 11/396,358, filed on Mar. 30, 2006, now Pat. No. 8,607,935.

(60) Provisional application No. 60/752,329, filed on Dec. 20, 2005.

(51) Int. Cl.
*A61B 17/00* (2006.01)

(52) U.S. Cl.
USPC ................. 606/1; 242/373; 254/334; 254/364

(58) Field of Classification Search
None
See application file for complete search history.

(56) References Cited

U.S. PATENT DOCUMENTS

| | | | |
|---|---|---|---|
| 2,168,209 A | 8/1939 | Haupt | |
| 3,820,752 A | 6/1974 | Oram | |
| 4,092,861 A * | 6/1978 | Fling | ................................ 73/311 |
| 4,494,177 A | 1/1985 | Matthews | |
| 4,527,942 A | 7/1985 | Smith | |
| 4,863,133 A | 9/1989 | Bonnell | |
| 4,973,015 A | 11/1990 | Beaucoup et al. | |
| 5,062,618 A | 11/1991 | Yamada et al. | |
| 5,149,029 A | 9/1992 | Smith | |
| 5,228,845 A | 7/1993 | Steele | |
| 5,402,801 A * | 4/1995 | Taylor | ........................... 128/898 |
| 5,450,766 A | 9/1995 | Holt | |
| 5,513,469 A | 5/1996 | Tajudeen et al. | |
| 5,634,872 A | 6/1997 | Brown et al. | |
| 5,931,048 A | 8/1999 | Slocum et al. | |

(Continued)

OTHER PUBLICATIONS

Vertut, Jean and Phillipe Coiffet, Robot Technology: *Teleoperation and Robotics Evolution and Development*, English translation, Prentice-Hall, Inc., Inglewood Cliffs, NJ, USA 1986, vol. 3A, 332 pages.

*Primary Examiner* — Lynsey Crandall

(57) ABSTRACT

In one embodiment of the invention, a patient side-system is provided that includes a column with a rail and a counterbalance subsystem. The patient side-system may further include a braking subsystem. The counterbalance subsystem includes a spring assembly coupled at one end to the column with a spring member, and a housing movably coupled to the rail. The housing includes a drum to receive the spring member and a plurality of roller elements to guide a movement of the spring member winding or unwinding on the drum. If present, the braking subsystem includes a first pulley rotatably coupled to the column, a second pulley with a locking mechanism spaced apart from the first pulley and rotatably coupled to the column, and at least one brake cable wrapped around the first pulley and the second pulley with ends coupled to the housing. The locking mechanism can set a position of the housing along the column.

18 Claims, 8 Drawing Sheets

(56) References Cited

U.S. PATENT DOCUMENTS

| | | |
|---|---|---|
| 6,132,368 A * | 10/2000 | Cooper .................... 600/102 |
| 6,646,431 B1 | 11/2003 | Parvez et al. |
| 6,863,435 B2 | 3/2005 | Moteki et al. |
| 7,160,413 B2 | 1/2007 | Kodaka et al. |
| 7,245,118 B2 | 7/2007 | Holt et al. |
| 7,276,894 B2 | 10/2007 | West |
| 7,428,855 B2 | 9/2008 | Duval |
| 7,476,072 B2 | 1/2009 | Tamura |
| 7,554,321 B2 | 6/2009 | Holt et al. |
| 8,607,935 B2 | 12/2013 | Goldberg et al. |
| 2003/0216715 A1* | 11/2003 | Moll et al. .................... 606/1 |
| 2004/0111183 A1* | 6/2004 | Sutherland et al. .......... 700/245 |

* cited by examiner

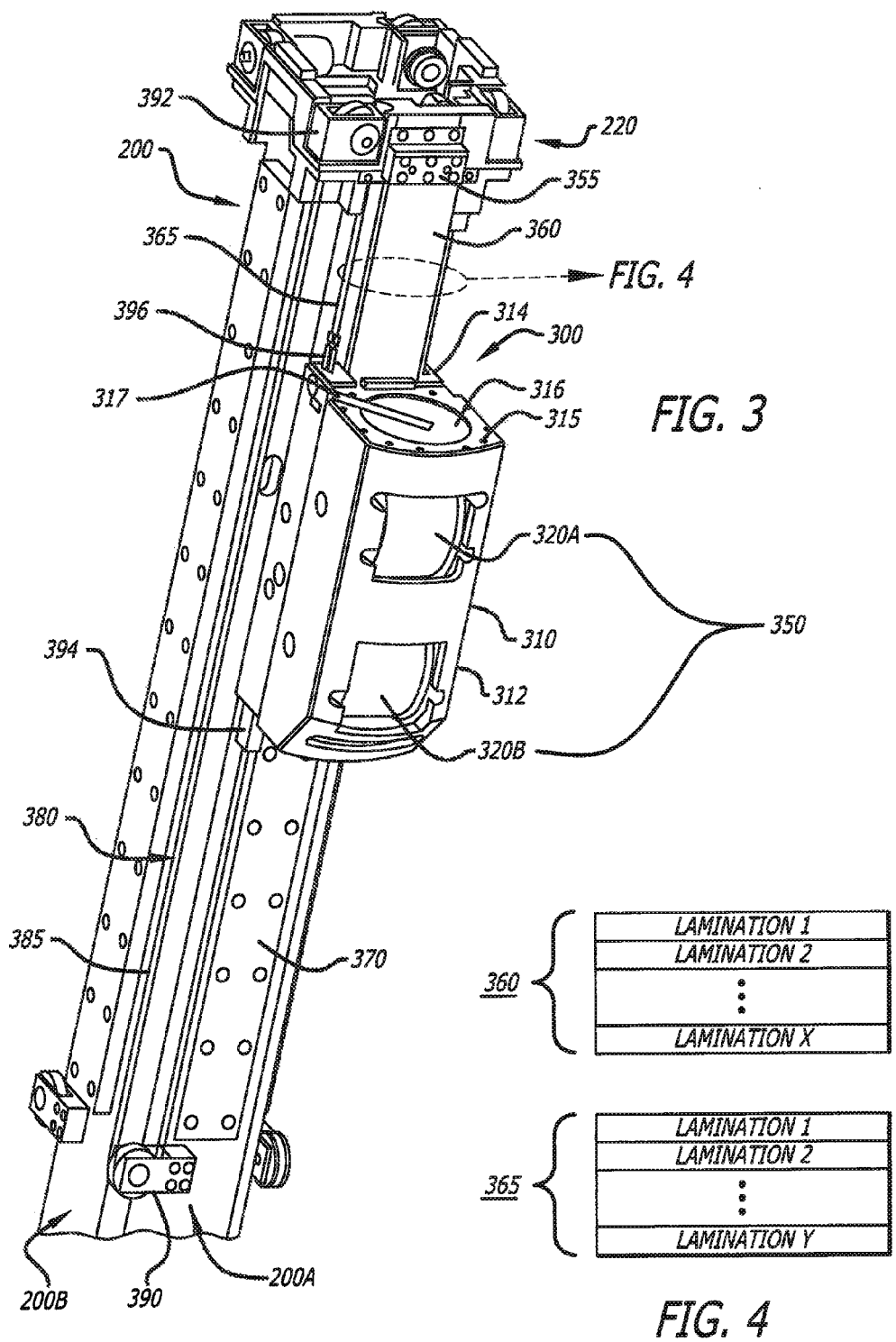

PATIENT SIDE SYSTEMS WITH A COUNTERBALANCE SUBSYSTEM

CROSS REFERENCE TO RELATED APPLICATION

This non-provisional patent application is a divisional and claims the benefit of U.S. patent application Ser. No. 11/396,358 entitled GUIDE SYSTEMS FOR LAMINATED SPRING ASSEMBLIES, filed by Randy Goldberg et al. on Mar. 30, 2006, pending. U.S. patent application Ser. No. 11/396,358 claims the benefit of U.S. Provisional Patent Application No. 60/752,329 entitled "GUIDE SYSTEM FOR LAMINATED CONSTANT FORCE SPRING ASSEMBLIES", filed on Dec. 20, 2005 by Randal P. Goldberg et al.

FIELD

The embodiments of the invention generally relate to robotic surgical systems. More particularly, the embodiments of the invention relate to a guide system for one or more laminated constant force spring (CFS) assemblies.

BACKGROUND

Previously, counterbalancing has been used for placement of robotic surgical arms in a static position prior to surgery. However, conventional counterbalancing mechanisms suffer from a number of disadvantages.

For instance, previously, robotic surgical arms have been positioned using conventional counterbalancing mechanisms. One conventional counterbalancing mechanism involves a constant force spring (CFS) assembly that controls the winding and unwinding of a spring member having at most three (3) laminations, namely three layers of material placed substantially in parallel and substantially in close physical proximity to each other, which wind and unwind from a common cylindrical drum.

This maximum number of laminations is partly due to the fact that, as the spring assembly is moved along a straight line of transport, the sections of the individual laminations (or layers) begin to separate from each other. Moreover, as the number of laminations increase, the separation becomes more pronounced, requiring more and more space for the spring assembly to operate. This poses a substantial problem where space for a counterbalance system is limited. Such limits are imposed by size requirements for the robotic surgical system.

In addition, the conventional counterbalancing mechanisms have failed to provide a high degree of safety, reliability and mechanical redundancy, since such mechanisms do not sufficiently spread the tension force in the event of a failure by one of the laminations within the spring assembly. In other words, the presence of two or three laminations within the spring assembly does not provide an acceptable level of safety because the failure of one lamination would result in a substantial reduction of the counterbalance force (e.g., 33-50% of the counterbalanced weight). In addition, carrying higher loads in a spring lamination adversely reduces the useful life of the spring assembly so that it will not likely survive for the entire expected life of the robotic surgical system.

BRIEF SUMMARY

The embodiments of the invention are summarized by the claims that follow below.

BRIEF DESCRIPTIONS OF THE DRAWINGS

The invention may best be understood by referring to the following description and accompanying drawings that are used to illustrate embodiments of the invention.

FIG. 1 is a block diagram of an embodiment of a robotic surgery system to perform minimally invasive robotic surgical procedures using one or more robotic surgical arms with a strap drive train.

FIG. 2 a perspective view of an embodiment of the robotic patient-side system of FIG. 1 with the one or more robotic surgical arms supported by set-up arms.

FIG. 3 is a perspective view of a first embodiment of the cart column of the robotic patient-side system of FIG. 2 that is used to control the positioning of one or more robotic surgical arms using a counterbalance subsystem and a braking subsystem.

FIG. 4 is a cross sectional view of the spring members illustrated in FIG. 3 winding and unwinding along the column.

DETAILED DESCRIPTION

The embodiments of the invention are related to a guide system for one or more laminated constant force spring assemblies. According to one embodiment of the invention, the guide system is based on rolling elements that can be bearing or bushing supported, to reduce friction present as the spring members move past the roller elements. As alternative embodiments of the invention, the guide system may be based on a static guide surface or a moving guide surface.

In the following description, certain terminology is used to describe features of the invention. For example, the term "lamination" is generally defined as a strip of material placed substantially in parallel and in close physical proximity with other strips of material to collectively form a spring member. The laminations in a spring member typically wind around a common drum. These strips of material are biased to gravitate toward a "wound" state. Examples of types of material forming the lamination may include, but are not limited or restricted to a strip of metal or metal alloy (e.g., stainless steel). According to one embodiment of the invention, the strips of material (or laminations) forming a spring member are affixed together only at one end, but remain in close proximity to each other due to this affixation and the tension applied to the laminations. According to another embodiment of the invention, the strips of material (or laminations) forming the spring member are affixed together at both ends. In either case, one end of the spring member is wound around a drum as part of a constant force spring (CFS) assembly.

A "spring assembly" is generally defined as one or more constant force spring (CFS) assemblies, each of which includes a spring member.

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

A. Robotic Surgical System

Figure 1:
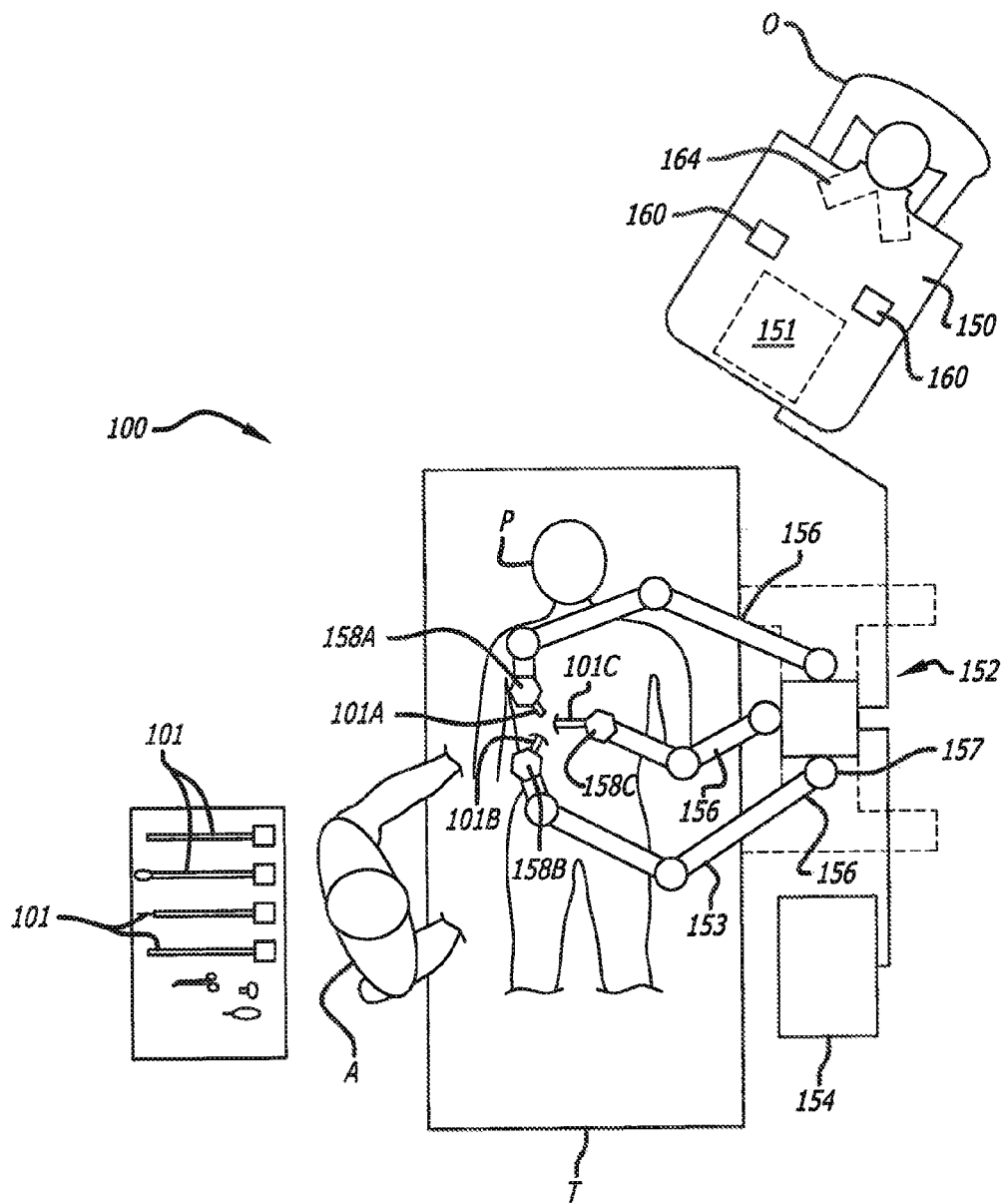

Referring now to FIG. 1, a block diagram of a robotic surgery system 100 is illustrated to perform minimally invasive robotic surgical procedures using one or more robotic arms 158. These robotic arms often support a surgical tool. For instance, a robotic surgical arm (e.g., the center robotic surgical arm 158C) is used to support a stereo or three-dimensional surgical image capture device 101C such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (e.g., stereotaxy), endoscopic procedures (e.g., laparoscopy, arthroscopy, thoracoscopy), and the like.

A user or operator O (generally a surgeon) performs a minimally invasive surgical procedure on patient P by manipulating control input devices 160 at a master control console 150. A computer 151 of the console 150 directs movement of robotically controlled endoscopic surgical instruments 101A-101C via control lines 159, effecting movement of the instruments using a robotic patient-side system 152 (also referred to as a "patient-side cart").

The robotic patient-side system 152 includes one or more robotic arms 158. Typically, the robotic patient-side system 152 includes at least three robotic surgical arms 158A-158C (generally referred to as robotic surgical arms 158) supported by corresponding positioning set-up arms 156. The central robotic surgical arm 158C may support an endoscopic camera 101C. The robotic surgical arms 158A and 158B to the left and right of center, may support tissue manipulation tools 101A and 101B, respectively.

Generally, as shown in this embodiment of the invention, the robotic patient-side system 152 includes a positioning portion and a driven portion. The positioning portion of the robotic patient-side system 152 remains in a fixed configuration during surgery while manipulating tissue. The driven portion of the robotic patient-side system 152 is actively articulated under the direction of the operator O generating control signals at the surgeon's console 150 during surgery. The "driven portion" of the robotic patient-side system 152 may include, but is not limited or restricted to robotic surgical arms 158A-158C.

As an exemplary embodiment, the "positioning portion" of the robotic patient-side system 152 that is in a fixed configuration during surgery may include, but is not limited or restricted to "set-up arms" 156. Each set-up arm 156 may include a plurality of links and a plurality of joints. Each set-up arm may mount via a first set-up-joint 157 to a housing 310 that may be moveably attached to a cart column 200, as is further described below with reference to FIG. 2.

An assistant A may assist in pre-positioning of the robotic patient-side system 152 relative to patient P as well as swapping tools or instruments 101 for alternative tool structures, and the like, while viewing the internal surgical site via an assistant's display 154.

B. Robotic Patient-Side System

Figure 2:
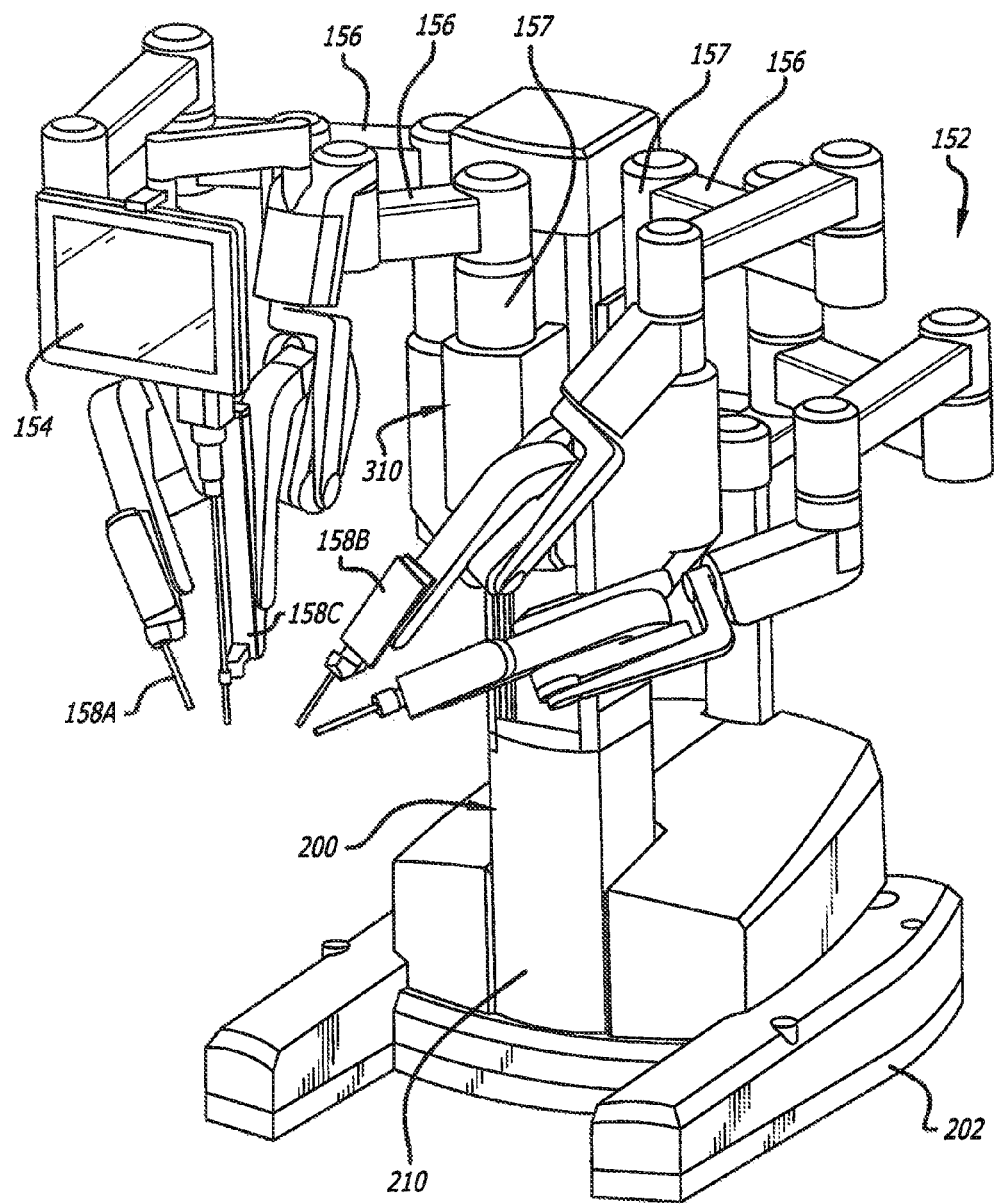

Referring now to FIG. 2, a perspective view of the robotic patient-side system 152 is illustrated. The robotic patient-side system 152 comprises a cart column 200 supported by a base 202. One or more robotic surgical arms 158 are respectively attached to one or more set-up arms 156 that are a part of the positioning portion of robotic patient-side system 152. Situated approximately at a central location on base 202, the cart column 200 includes a protective cover 210 that protects components of a counterbalance subsystem and a braking subsystem (described below) from contaminants.

Excluding a monitor arm 154, each robotic surgical arm 158 is used to control robotic surgical tools 101A-101C. Moreover, each robotic surgical arm 158 is coupled to a set-up arm 156 that is in turn coupled to a carriage housing 310 in one embodiment of the invention, as described below with reference to FIG. 3. The one or more robotic surgical arms 158 are each supported by their respective set-up arm 156, as is illustrated in FIG. 2.

The robotic patient-side system 152 generally has dimensions suitable for transporting between operating rooms. It typically can fit through standard operating room doors and onto standard hospital elevators. The robotic patient-side system 152 may have a weight and a wheel (or other transportation) system that allows the cart to be positioned adjacent an operating table by a single attendant. The robotic patient-side system 152 may be sufficiently stable during transport to avoid tipping, and to easily withstand overturning moments that may be imposed at the ends of the robotic arms during use.

Referring to FIG. 3, a perspective view of the cart column 200 of the robotic patient-side system 152 that is used to control the positioning of one or more set-up arms is shown. Cart column 200 is illustrated in rectangular form with each rectangular side 200A-200D featuring a counterbalance subsystem 300 vertically adjusted along a rail 370 and a braking subsystem 380.

Figure 5:
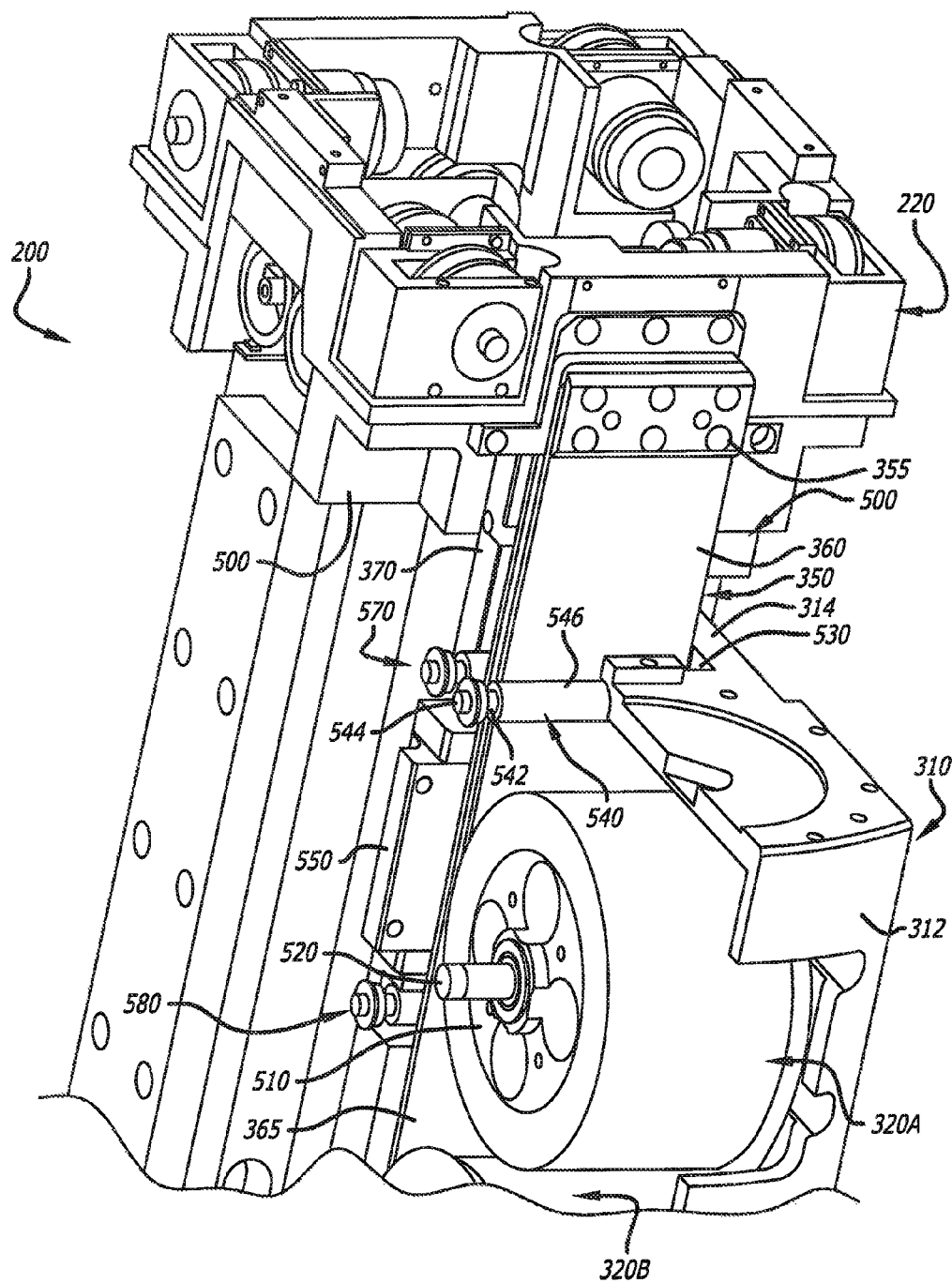
FIG. 5 is a cut-away view of an embodiment of the carriage housing and the spring of FIG. 3.

According to this embodiment of the invention, counterbalance subsystem 300 comprises a carriage housing 310 that includes a first housing portion 312 and a second housing portion 314 (collectively housing portions 312 and 314 form the carriage housing 310). The second housing portion 314 is adapted to cover and protect one or more linear bearing assemblies that enable mobility along the rail 370 and corresponding roller elements as shown in FIG. 5.

As shown, first housing portion 312 is adapted to house one or more laminated constant force spring (CFS) assemblies 320A-320N (N≥1) that comprise the spring assembly 350. Carriage housing 310 is moved in a substantially vertical direction supported by the winding and unwinding of one or more spring members of the spring assembly 350, such as CFS assemblies 320A 320B. In other words, the winding and unwinding operations by the CFS assemblies 320A-320B exert a relatively constant upward force, counterbalancing the weight of set-up and robotic arms (such as set-up arm 156 illustrated in FIG. 2, which adjusts the pre-surgery positioning of the corresponding robotic arm 158). As the number of links and joints in each set-up arm may vary, the weight between set-up arms may differ. Thus, a differing number of laminations may be used in each of the one or more spring members for each set up arm as their weights may differ.

The first housing portion 312 comprises a top surface 315 that includes a recessed area (also referred to as a pocket) 316 with a slot 317. More specifically, an end of the set-up arm (not shown) is mounted on the top surface 315 and secured to the carriage housing by fasteners such as bolts. The slot (also referred to as a clearance hole) 317 may be used to feed electrical cabling through the set-up arm to control the robotic surgical arm. As an optional embodiment, it is contemplated that the set-up arm may be secured to the first housing portion 312 by any other attachment mechanism and, in fact, may be secured to other surfaces of the carriage housing 310 besides its top surface 315.

Referring still to FIG. 3, the vertical position of the carriage housing 310 along cart column 200 is set by the braking subsystem 380, which features two brake cables 385 that rotate around a first pulley 390 and a locking pulley 392. One end of each of the two brake cables 385 is coupled to a bottom side of the carriage housing 310 via a spring loaded tensioner 394, as is illustrated in FIG. 3. An opposite end of each of the two brake cables 385 is coupled to a top side of the carriage housing 310 via turnbuckles 396, as is also illustrated in FIG. 3. This allows the cable tension in each of the brake cables 385 to be separately adjusted and maintained during operation.

The locking pulley 392 allows the cables 385 to be rotated, but has a locking mechanism that halts further rotation of the cables 385 until unlocked. By halting rotation by the locking pulley 392, the carriage housing 310 is retained at the desired height by the cables 385. For instance, when the carriage housing 310 is lowered vertically down the rail 370, the cables 385 and pulleys 390,392, are rotated in a clockwise direction. Likewise, when the carriage housing 310 is vertically translated upward toward a top cap portion 220 of the cart column 200, the cables 385 and pulleys 390,392, undergo a counter-clockwise rotation.

Referring to FIGS. 3 and 4, an exemplary embodiment of one or more spring members 360,365 for the spring assembly 350 is shown. The one or more spring members 360,365 are fed through an opening between the first housing 312 and the second housing 314 of the carriage housing 310. In this exemplary embodiment of the invention, the spring assembly 350 includes the first CFS assembly 320A with the first spring member 360 and the second CFS assembly 320B with the second spring member 365.

Herein, each of the spring members 360 and 365 include a plurality of laminations, such as four or more layers of material (laminations) with a first end 355 of the spring assembly 350 being attached to the top cap portion 220 of cart column 200 by bolting, laser welding, or any other method of attachment. As an example, the first spring member 360 includes at least seven laminations and perhaps up to nine laminations. The second spring member 365 includes at least seven laminations or perhaps ranges between seven to nine laminations. The number of laminations selected is based in part on the weight of the arms that are to be supported by the carriage housing 310. In one embodiment of the invention, each layer of lamination is a strip of stainless steel approximately three (3) inches wide, sixty-seven to seventy-five (67-75) inches long, and twenty-thousandths of an inch (0.020) thick.

Of course, it is contemplated that spring assembly 350 may comprise a plurality of CFS assemblies with multiple spring members having multiple laminations or a single CFS assembly with a single spring member having at least four laminations or most likely more than or equal to seven laminations.

Referring now to FIG. 5, a cut-away view of a portion of the carriage housing 310 and the spring assembly 350 of FIG. 3 are illustrated. A stop barrier 500 is positioned below the top cap portion 220 of the cart column 200 into order preclude movement of the carriage housing 310 above a predetermined height. This prevents the carriage housing 310 from lifting off the guide rail 370. As shown, the stop barrier 500 is a reinforced member that would come into contact with a top surface of the second housing 314 if the carriage housing 310 is lifted above a predetermined maximum height.

As previously described, the second housing 314 of the carriage housing 310 is movably coupled to the rail 370 mounted on the cart column 200. More specifically, first housing 312 houses a number of components, including but not limited to one or more CFS assemblies 320, namely the first and second CFS assemblies 320A and 320B, and a first roller element 540. The first CFS assembly 320A includes a cylindrical drum 510 supported by a shaft 520 positioned laterally across first housing 312. The cylindrical drum 510 is rotatably coupled to the first and second housing portions 312,314 of the carriage housing 310 by the shaft 520. Similarly, the second CFS assembly 320B is positioned below the first CFS assembly 320A and features the same general construction.

One or more spring members 360,365 are fed through opening 530 between the first and second housings 312 and 314. According to one embodiment of the invention, the first spring member 360 is aligned and in parallel with the second spring member 365. The first spring member 360 includes multiple laminations, such as seven-to-nine laminations as an illustrative example, that are wound around the drum 510 of the first CFS assembly 320A. Likewise, the second spring member 365 includes multiple laminations, such as seven-to-nine laminations for example, that are wound around a drum (not shown in FIG. 5, see drum 615 in FIG. 6 for example) of the second CFS assembly 320B.

The first roller element 540 comprises a guide shaft 542 placed laterally within carriage housing 310 and generally in parallel with the shaft 520. Bearings 544 are placed at the ends of the guide shaft 542 and rotationally coupled to an inner surface of the first housing 312 so that the guide shaft 542 can be rotated as first spring member 360 passes. A roller 546 is placed over a substantial portion of the guide shaft 542 to apply pressure and prevent contact of lamination 1 (referring to FIG. 4) of the first spring member 360 with the second housing 312.

Second housing 314 houses one or more linear bearing assemblies that are coupled to at least one inner wall of second housing 314 and are movably coupled to the rail 370. For instance, according to one embodiment of the invention, a first linear bearing assembly 550 is vertically oriented within second housing 314 at a location adjacent to the first CFS assembly 320A. A second linear bearing assembly 660 (not shown in FIG. 5, see FIG. 6) is vertically oriented within second housing 314 at a location adjacent to the second CFS assembly 320B.

A pair of roller elements 570 and 580 is positioned above and below first linear bearing assembly 550, to assist in the guiding of spring members. As shown, the second roller element 570 applies pressure to prevent contact of lamination y of the second spring member 365 with the first housing 312 or the linear bearing assembly 550. The first roller element 540 applies a force against the first spring member 360, while concurrently, the second roller element 570 applies a force against the second spring member 365.

The third roller element 580 is positioned below first linear bearing assembly 550 and below shaft 520 toward a bottom curvature of drum 510. The third roller element 580 applies a force against the second spring member 365 upon its passing to or from the second CFS assembly 320B.

Figure 6:
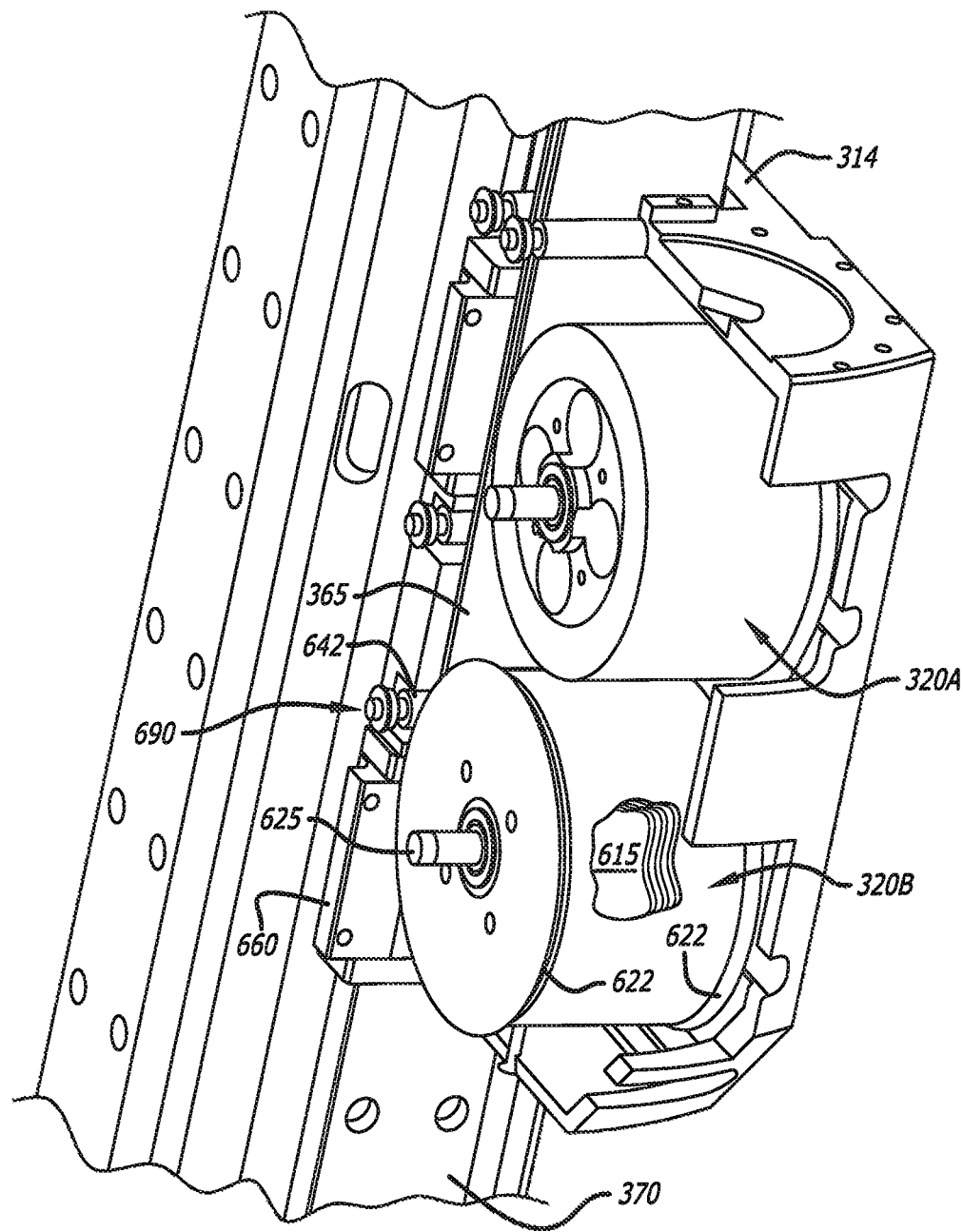
FIG. 6 is a more detailed cut away view of an embodiment of the carriage housing.
Figure 7:
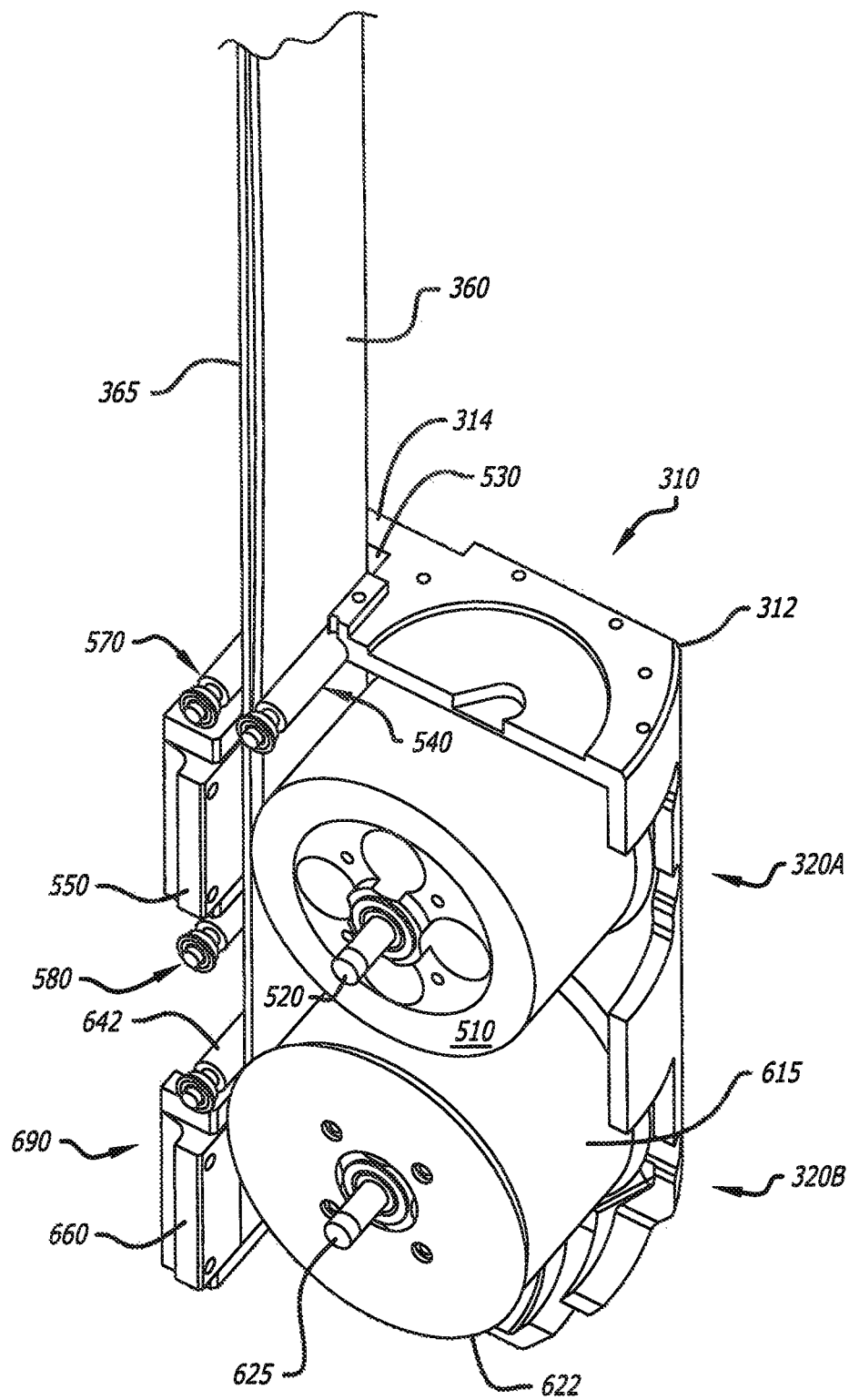
FIG. 7 is a further illustration of the guide system as shown in FIGS. 5 and 6.

Referring to FIG. 6, a more detailed cut-away view of an embodiment of the carriage housing 310 is shown. FIG. 7 provides a further illustration of the guide system as well. Second housing 314 houses the second linear bearing assembly 660 that is coupled to at least one inner wall of second housing 314 and are movably coupled to the rail 370. Second linear bearing assembly 660 is vertically positioned adjacent to second CFS assembly 320B. Second linear bearing assembly 660 provides additional support for carriage housing 310.

A fourth roller element 690 is positioned above the second linear bearing assembly 660 and above shaft 625 toward a top curvature of drum 615. As illustrated in FIG. 6, the cylindrical drum 615 is rotatably coupled to the first and second housing portions 312, 314 of the carriage housing 310 by the shaft 625. The fourth roller element 690 features a roller 692 that applies a force against the second spring member 365 upon its passing to or from second CFS assembly 320B. This assists in maintaining minimum separation distance of laminations forming second spring member 365. Moreover, second CFS assembly 320B includes a pair of flanges 622 placed on both sides of drum 615 to prevent laminations from sliding off drum 615. Of course, although not shown, flanges may be used by the second CFS assembly 320A as well.

Figure 8:
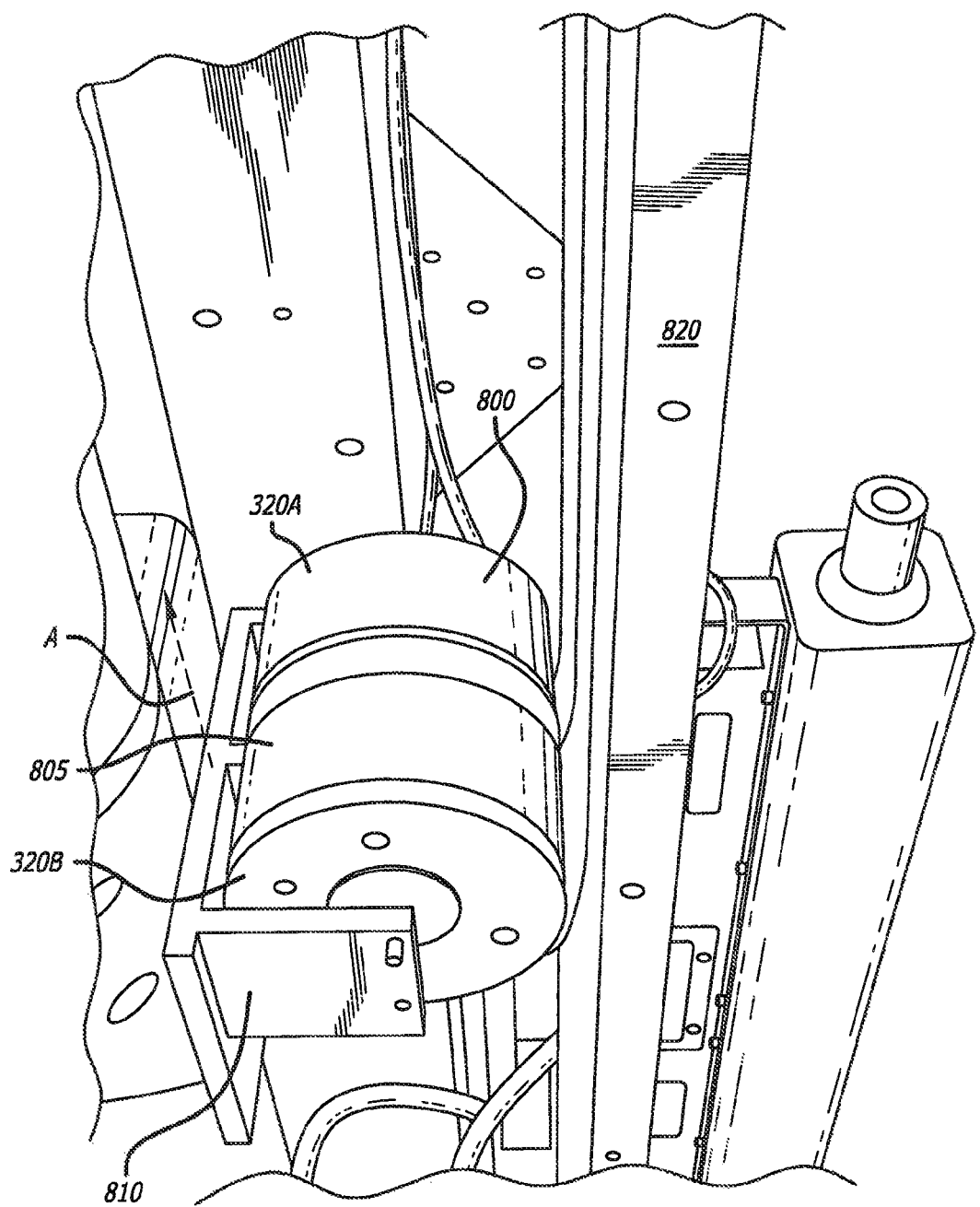
FIG. 8 is a second embodiment of the robotic patient-side system of FIG. 2 that is used to control the positioning of one or more robotic surgical arms using a static guide surface.

Referring now to FIG. 8, a second embodiment of the guide system utilized by the robotic patient-side system 152 of FIG. 2 is shown. According to this embodiment of the invention, chassis housing 810 comprises a plurality of CFS assemblies 320A and 320B arranged side-by-side, where each CFS assembly 320A and 320B is adapted to receive a separate spring member 800 and 805 featuring one or more laminations. The chassis housing 810 may be translated vertically as represented by arrow A.

In lieu of roller elements as described above, a guide wall 820 is positioned along cart column 200 so as to exert a force along the straight section of spring members 800 and 805. This force prevents the laminations of the spring members 800 and 805 from separating. As shown, there is no relative motion between the surface of the guide wall 820 and spring members 800 and 805.

Referring to FIGS. 4 and 5, it can be noted that in this earlier embodiment, lamination 1 of the second spring member 365 performs this same function, acting as a guide wall exerting a force along the laminations of the first spring member 360. Contact is between lamination 1 of the second spring member 365 and lamination x of the first spring member 360.

Figure 9:
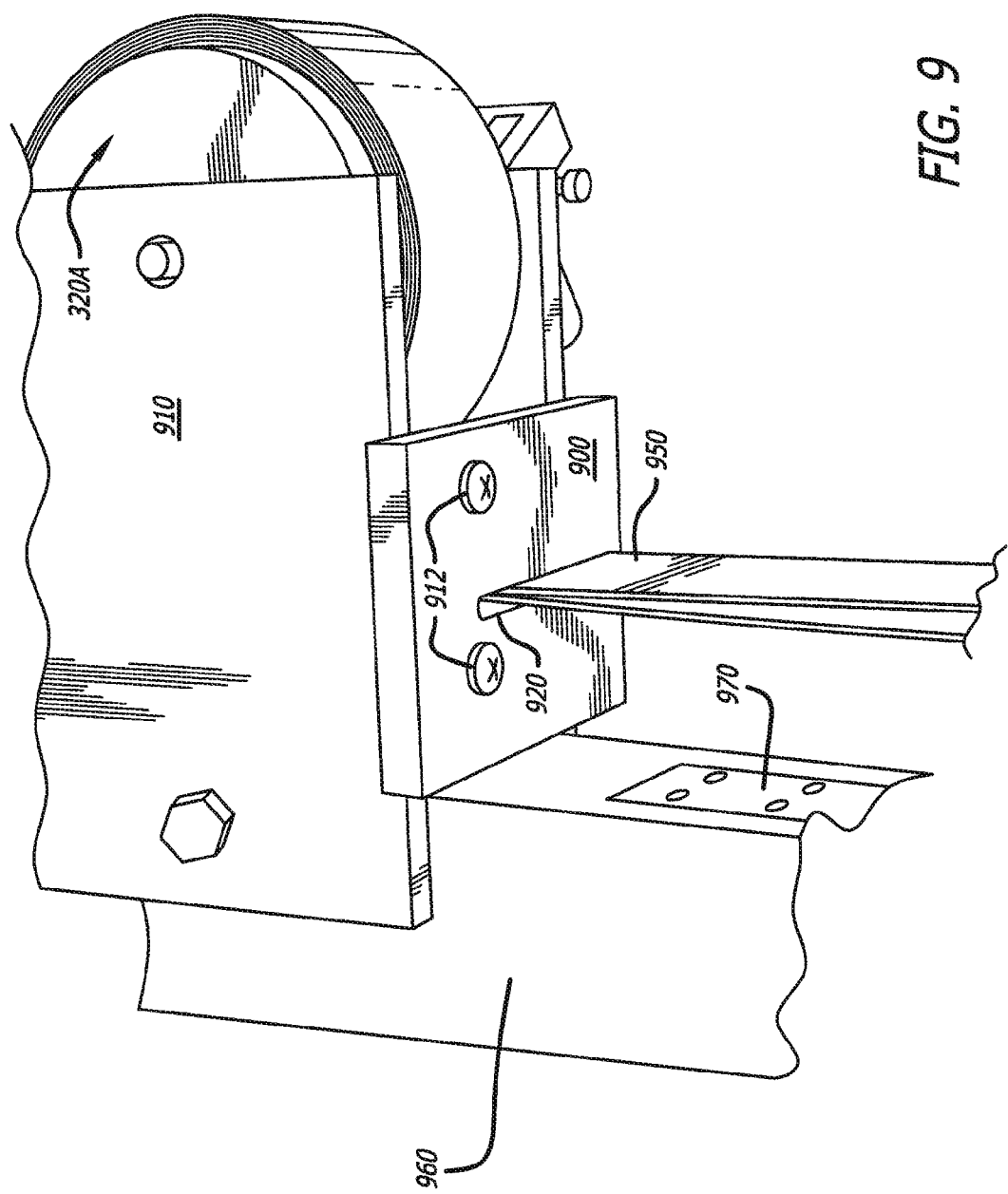
FIG. 9 is a third embodiment of the robotic patient-side system of FIG. 2 that is used to control the positioning of one or more robotic surgical arms using a moving guide surface.

Referring to FIG. 9, a third embodiment of a guide system utilized by the robotic patient-side system 152 of FIG. 2 is shown. According to this embodiment of the invention, a guide system comprises a guide surface 900 placed on a chassis housing 910 that is adapted to house one or more CFS assemblies (e.g., CFS assembly 320A). The guide surface 900 is coupled to the chassis housing 910 by a pair of fasteners 912, as is illustrated in FIG. 9.

CFS assembly 320A is adapted to receive a spring member 950 that is fed through an opening 920 in the guide surface 900. The opening 920 is sized with an appropriate width and length to deter separation of the laminations forming the spring member 950.

The chassis housing 910 may be coupled to a column 960 in a fixed position near the top of the column. The spring member 950 extends downward from the chassis housing 910 along the length of the column 960. The end of the spring member 950 not wound onto the drum may couple directly to a set-up arm (not shown in FIG. 9, see set-up arm 156 in FIGS. 1-2). The set up arm is moved vertically along the column 960 to adjust its height to support a robotic surgical arm in a proper position. The set-up arm may be moveably coupled to a guide rail 970 along the column 960. The spring member 950 unwinds from the drum of the CFS assembly 320A when its end is pulled downward with the set-up arm. The spring member 950 winds up onto the drum when its end is pushed upwards with the set-up arm.

While only one CFS assembly 320A including one spring member 950 is shown in FIG. 9, it is to be understood that more than one CFS assembly and one spring member may be used in the third embodiment of the invention.

In short, the embodiments of the invention are directed to a system to guide and constrain the movement of a spring assembly including (constant force) spring members. As previously mentioned, one of the drawbacks of multiple laminations for each spring member is that, as the laminations are moved through large extensions, the individual laminations (in the straight section of spring) spread out from one another. As the number of laminations is increased, this effect becomes more pronounced, requiring more and more space for the springs to operate.

The invention includes several methods for guiding the straight section of these laminations as the spring assembly is extended, allowing a more compact overall volume for packaging and operation of the spring members of the spring assembly. Each of the guiding methods prevents the outer laminations from separating too far away from the inside lamination. The extra material buildup is then taken up in loops around the spring drum. Since the diameter of the spring members on the drum varies inversely with the amount of buildup, the net volume taken up by the spring material around the drum does not change drastically, even with relatively long extensions and large numbers of laminations. This allows for compact packaging and operation of assemblies with a large number of individual laminations over large extensions.

The method of guiding can take several different forms. Possible categories include a static guide surface, a moving guide surface, or roller guides. Static and moving surfaces refer to motion of the guide surface relative to the free end of the spring. A static guide surface is essentially a wall that exerts force along the straight section of the spring material, preventing the laminations from separating. There is no relative movement between the spring material and the surface, so there is minimal increase in friction (see FIG. 8). A moving guide surface involves feeding the spring past a surface. Here, there is relative motion between the guide surface and spring (See FIG. 9). Finally, roller elements can be used instead of the moving guide surface (See FIGS. 3-7). In addition, these methods of guiding the laminations hold for cases where the spring drum is attached to either the fixed or moving component in the assembly.

Currently two forms of these guiding mechanisms have been implemented with large lamination constant force spring assemblies in a system. In this system implementation (see FIGS. 5-7), two constant force spring (CFS) members, each consisting of 7 to 9 laminations, are mounted within the carriage housing. The carriage housing, which translates vertically along the cart column on a linear bearing, supports a set-up arm. The laminations of the first CFS assembly are guided by the inside (front) lamination of the second CFS assembly (the second CFS assembly acts as a static guide surface for the top assembly). The laminations of the second CFS assembly are guided by bearing supported roller shafts, to prevent the springs from spreading back towards the cart column and rubbing on the linear bearing trucks. In this system implementation, the free ends of both CFS assemblies are rigidly fixed to the top of the cart column.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art after reading this disclosure. Instead, the embodiments of the invention should be construed according to the claims that follow below.

What is claimed is:

1. A patient side-system comprising:
   a column including a rail; and
   a counterbalance subsystem including
      a spring assembly coupled at one end to the column, the spring assembly including at least one spring member composed of a plurality of laminations, and
      a housing coupled to the column, the housing including
         at least one drum to receive the at least one spring member, and
         a plurality of roller elements adapted to guide a movement of the at least one spring member winding onto or unwinding off of the drum, the plurality of roller elements further adapted to press against one or more of the plurality of laminations of the at least one spring member to prevent lamination separation.

2. The patient side-system of claim 1, further comprising:
   a braking subsystem including
      a first pulley rotatably coupled to the column,
      a second pulley spaced apart from the first pulley and rotatably coupled to the column,
      at least one brake cable wrapped around the first pulley and the second pulley, the at least one brake cable having a first end and a second end coupled to the housing, and
      wherein the second pulley has a locking mechanism to halt its rotation and movement of the at least one brake cable to set a position of the housing along the column between the first pulley and the second pulley.

3. The patient side-system of claim 1, wherein
   the housing is moveably coupled to the rail of the column.

4. The patient side-system of claim 3, further comprising:
   a set-up arm coupled to the housing;
   a robotic surgical arm coupled to the set-up arm, the robotic surgical arm to support a surgical tool; and
   wherein the set-up arm to support the robotic surgical arm.

5. The patient side-system of claim 4, wherein
   the set-up arm includes one or more links and one or more joints.

6. The patient side-system of claim 4, wherein
   the surgical tool is a stereo surgical image capture device.

7. The patient side-system of claim 4, wherein
   the surgical tool is a tissue manipulation tool.

8. The patient side-system of claim 2, wherein
   the column further includes a protective cover to protect the counterbalance subsystem and the braking subsystem.

9. The patient side-system of claim 1, wherein
   the housing is fixedly coupled to the column.

10. The patient side-system of claim 9, further comprising:
    a set-up arm coupled to one end of a spring member, the set-up arm moveably coupled to the rail of the column;
    a robotic surgical arm coupled to the set-up arm, the robotic surgical arm to support a surgical tool; and
    wherein the set-up arm to support the robotic surgical arm.

11. The patient side-system of claim 10, wherein
    the set-up arm includes one or more links and one or more joints.

12. The patient side-system of claim 1, wherein
    the housing comprises
       a first housing portion, the first housing portion adapted to house one or more laminated constant force spring assemblies each including the spring member and the drum, and the plurality of roller elements, and
       a second housing portion, the second housing portion adapted to cover and protect one or more linear bearing assemblies that enable mobility along the rail.

13. The patient side-system of claim 1, further comprising:
    a base coupled to the column, the base to support the column.

14. The patient side-system of claim 10, wherein
    the surgical tool is a stereo surgical image capture device.

15. The patient side-system of claim 10, wherein
    the surgical tool is a tissue manipulation tool.

16. The patient side-system of claim 10, further comprising:
    a braking subsystem including
       a first pulley rotatably coupled to the column,
       a second pulley spaced apart from the first pulley and rotatably coupled to the column,
       at least one brake cable wrapped around the first pulley and the second pulley, the at least one brake cable having a first end and a second end coupled to the setup arm, and
       wherein the second pulley has a locking mechanism to halt its rotation and movement of the at least one brake cable to set a position of the set up arm along the column between the first pulley and the second pulley.

17. The patient side-system of claim 16, wherein
    the column further includes a protective cover to protect the counterbalance subsystem and the braking subsystem.

18. The patient side-system of claim 1, wherein
    the at least one drum is rotatably coupled to housing by a shaft.

* * * * *